(12) United States Patent
Onuma

(10) Patent No.: US 11,692,966 B2
(45) Date of Patent: Jul. 4, 2023

(54) SAMPLE COMPONENT SEPARATION ANALYSIS METHOD

(71) Applicant: ARKRAY, Inc., Kyoto (JP)

(72) Inventor: Naotsugu Onuma, Kyoto (JP)

(73) Assignee: ARKRAY, INC., Kyoto (JP)

( * ) Notice: Subject to any disclaimer, the term of this patent is extended or adjusted under 35 U.S.C. 154(b) by 398 days.

(21) Appl. No.: 16/905,075

(22) Filed: Jun. 18, 2020

(65) Prior Publication Data

US 2020/0400611 A1 Dec. 24, 2020

(30) Foreign Application Priority Data

Jun. 21, 2019 (JP) .................................. 2019-115641
Jun. 15, 2020 (JP) .................................. 2020-103262

(51) Int. Cl.
*G01N 27/447* (2006.01)
*G01N 33/49* (2006.01)
*G01N 27/416* (2006.01)

(52) U.S. Cl.
CPC ... *G01N 27/44721* (2013.01); *G01N 27/4163* (2013.01); *G01N 27/44747* (2013.01); *G01N 33/491* (2013.01)

(58) Field of Classification Search
None
See application file for complete search history.

(56) References Cited

FOREIGN PATENT DOCUMENTS

| EP | 3315959 A1 | 5/2018 |
| EP | 3477292 A1 | 5/2019 |
| JP | 2013-174625 A | 9/2013 |
| JP | 2018-072336 A | 5/2018 |

OTHER PUBLICATIONS

Extended European Search Report issued in corresponding European Patent Application No. 20181099.1 dated Nov. 20, 2020.

*Primary Examiner* — J. Christopher Ball
(74) *Attorney, Agent, or Firm* — Morgan, Lewis & Bockius LLP

(57) ABSTRACT

There is provided a separation analysis method for analyzing a sample component s included in a sample liquid by introducing the sample liquid into a separation flow path filled with a flow path liquid, the method comprising: obtaining a correction factor representing a proportion of a time period from the first point in time when the sample liquid is introduced into the separation flow path, to the second point in time when an interface between the flow path liquid and the sample liquid reaches a predetermined position at the separation flow path, with respect to a time period from the first point in time to the third point in time when an optical characteristic value of the sample component is measured at the predetermined position, and correcting the measured optical characteristic value with the correction factor.

14 Claims, 15 Drawing Sheets

SAMPLE COMPONENT SEPARATION ANALYSIS METHOD

CROSS-REFERENCE TO RELATED APPLICATION

This application claims priority under 35 USC 119 from Japanese Patent Application Nos. 2019-115641, filed on Jun. 21, 2019 and 2020-103262, filed on Jun. 15, 2020, the disclosure of which is incorporated by reference herein.

BACKGROUND

Technical Field

The present invention relates to a separation analysis method for sample components.

Related Art

In a component separation analyzing system using continuous specimen introduction such as capillary electrophoresis or the like, there is a technique of creating, as an original waveform, a curve obtained by plotting detected data, such as absorbance or the like acquired by a detector, on the vertical axis and time on the horizontal axis, and carrying out separation analysis by using a differential waveform, such as an electropherogram or the like, obtained by differentiating the original waveform over time.

The respective peaks appearing in the differential waveform correspond to the respective components included in the introduced specimen. The components can be identified by the differences in the times at which the tops of the respective peaks are recognized. Moreover, an area of a peak in the electropherogram is an index of an amount of the component present in the specimen. For example, a differential waveform of a hemoglobin measuring system in accordance with continuous specimen introduction that uses blood as a specimen may have a shape such as shown in Japanese Patent Application Laid-Open (JP-A) No. 2018-72336 and JP-A No. 2013-174625.

Separation analysis of hemoglobin by capillary electrophoresis is carried out by causing a sample liquid including a hemoglobin-containing specimen to migrate toward a cathode in a capillary channel, by utilizing the fact that hemoglobin molecular surfaces are positively charged. In this case, in order to prevent the hemoglobin molecules from being adsorbed at the inner wall of the capillary channel, an anionic polymer such as chondroitin sulfate or the like is included in the migration liquid, and the inner wall of the capillary channel is covered by the negatively-charged molecules. However, even if the same sample is measured, there are cases in which, for some reason, the peak areas of the respective components change each time measurement is carried out. Therefore, accurate separation analysis cannot be carried out.

SUMMARY

The present disclosure provides a separation analysis method for analyzing a sample component included in a sample liquid by introducing the sample liquid into a separation flow path filled with a flow path liquid, the method including: obtaining a correction factor representing a proportion of a time period from a first point in time when the sample liquid is introduced into the separation flow path, to a second point in time when an interface between the flow path liquid and the sample liquid reaches a predetermined position at the separation flow path, with respect to a time period from the first point in time to a third point in time when an optical characteristic value of the sample component is measured at the predetermined position, and correcting the measured optical characteristic value with the correction factor.

In an embodied aspect of the present invention, respective components can be measured correctly even if the concentration ratio, which depends on a speed difference between the speed at which the sample liquid flows through the separation flow path and the speed at which a sample component flows through the separation flow path, varies due to changes in a reagent concentration or due to environmental factors such as an environmental temperature or the like.

BRIEF DESCRIPTION OF THE DRAWINGS

Exemplary embodiments will be described in detail based on the following figures, wherein.

DETAILED DESCRIPTION

Figure 1:
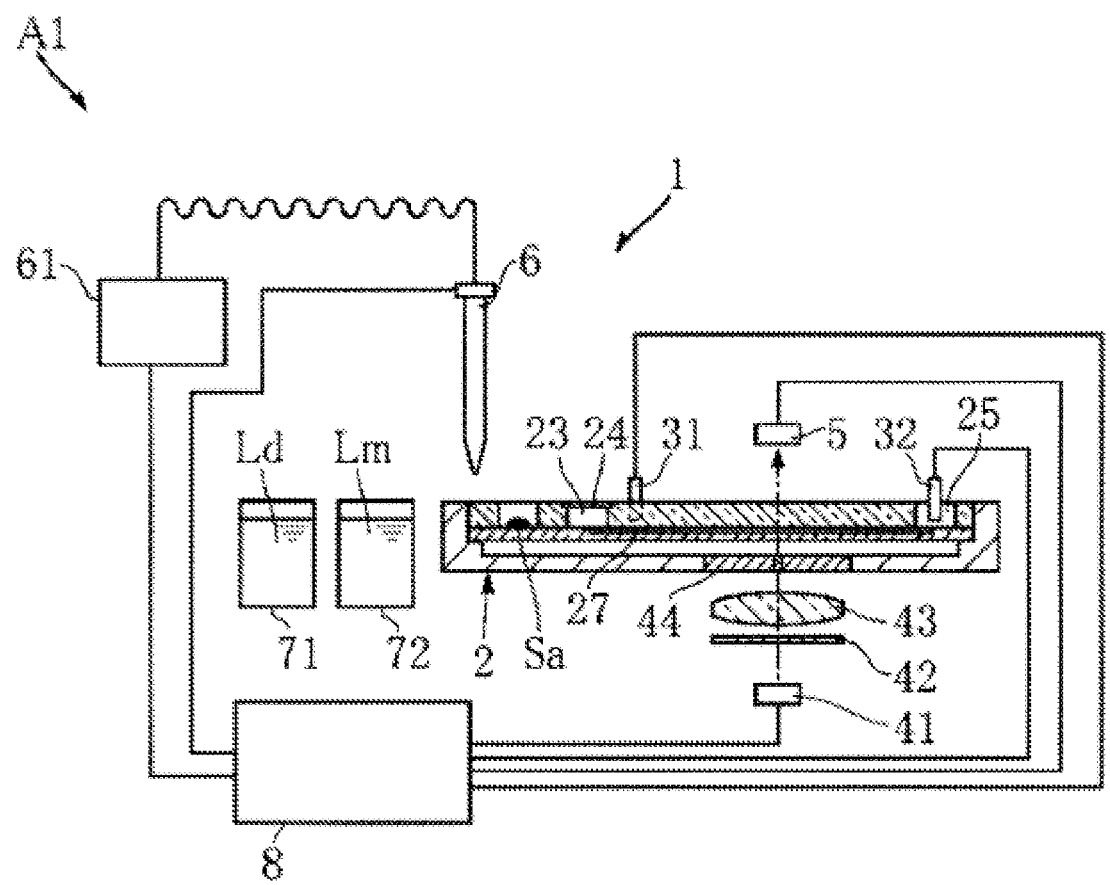
FIG. 1 is a system schematic drawing showing an example of an analyzing system.

In a separation analysis method of the present disclosure for analyzing a sample component included in a sample liquid by introducing the sample liquid into a separation flow path filled with a flow path liquid, a correction factor representing a proportion of a time period from a first point in time when the sample liquid is introduced into the separation flow path, to a second point in time when an interface between the flow path liquid and the sample liquid reaches a predetermined position at the separation flow path, with respect to a time period from the first point in time to a third point in time when an optical characteristic value of the sample component is measured at the predetermined position is obtained. In other words, a correction factor representing a proportion of a speed at which the sample component flows through the separation flow path, with respect to a speed at which the sample liquid flows through the separation flow path is obtained. Then, the measured optical characteristic value is corrected with the correction factor.

It suffices for the separation analysis method to be a method that carries out separation analysis based on the differences in the moving speeds of the sample components flowing through the flow path. The respective sample components included in the sample flow through the separation flow path at respective moving speeds corresponding to the properties of the respective sample components. Therefore, the respective sample components are separated as they flow through the separation flow path. By detecting the respective components separated in the separation flow path, the respective components are identified and/or quantified. The separation analysis method may be, for example, electrophoresis, liquid chromatography, or gas chromatography. The separation analysis method can be selected appropriately in consideration of the types and the properties of the sample and the sample components, and the like. The present invention is particularly useful in separation analysis methods in which the moving speeds of the sample components within the flow path vary due to effects of temperature or environmental effects in particular. The separation flow path is also called a column or a capillary channel, in accordance with the separation method.

Capillary electrophoresis is particularly preferable as the separation analysis method. The separating conditions of capillary electrophoresis can be changed appropriately in consideration of the type and the properties of the sample, the types of the sample components to be separated, the properties of the sample components, and the like. For example, in a case of carrying out separation in accordance with the difference in positive charge amounts of sample components, of the anode and the cathode provided at the both ends of the capillary channel respectively, the sample liquid migrates toward the cathode. Accordingly, it is desirable for the migration liquid to include an anionic polymer. The anionic polymer is desirably chondroitin sulfate. Further, in a case in which, for example, separation is carried out in accordance with the difference in negative charge amounts of sample components, of the anode and the cathode provided at the both ends of the capillary channel respectively, the sample liquid migrates toward the anode. Accordingly, it is desirable for the migration liquid to include a cationic polymer.

The time distribution of the amount of change in the optical characteristic value per unit time is shown in a graph with the amount of change per unit time in the optical characteristic value being on the vertical axis, and the time corresponding to the amount of change per unit time in the optical characteristic value, being on the horizontal axis. The time distribution of the amount of change in the optical characteristic value per unit time encompasses an electropherogram obtained from the measurement results of capillary electrophoresis, or a chromatogram obtained from the measurement results of liquid chromatography or gas chromatography. The point in time at which analysis starts may be the reference point of the horizontal axis. Otherwise, the point in time at which a sample component is introduced into the separation flow path may be used as the reference point of the horizontal axis. In a capillary electrophoresis method, the electropherogram may be prepared by using the point in time at which voltage is applied as the reference point of the horizontal axis.

In the separation analysis method, first, before the separation analysis of the sample components, the separation flow path is filled with a flow path liquid. The flow path liquid is, for example, a migration liquid in the capillary electrophoresis method, and an eluent in liquid chromatography. The method of filling the capillary channel with the migration liquid can be selected appropriately. For example, the capillary channel may be filled with the migration liquid by feeding the migration liquid into the capillary channel from a migration liquid reservoir connected to the capillary channel.

Then, a sample liquid including sample components is introduced continuously into the separation flow path having a detecting section. The method of introducing the sample liquid into the separation flow path can be selected appropriately. For example, in a case of separation to analyze hemoglobin molecules by capillary electrophoresis, a pair of electrodes are placed at the both ends of the capillary channel filled with the migration liquid. Then, the sample liquid is made to contact the anode side end portion of the capillary channel. Then, when voltage is applied to the capillary channel and electrophoresis starts, the migration liquid at the interior of the capillary channel flows from the anode side to the cathode side as an electro-osmotic flow. Then, accompanying the flowing of the migration liquid from the anode side to the cathode side, the sample liquid including the hemoglobin components is introduced from the anode side of the capillary channel at the speed of the electro-osmotic flow. While the interface between the sample liquid and the migration liquid filling the capillary channel is maintained as is, the sample liquid flows through the capillary channel at the speed of the electro-osmotic flow, and the interface reaches the detecting section provided at the capillary channel. Simultaneously, the hemoglobin components, which have been introduced into the capillary channel at the speed of the electro-osmotic flow, flow through the capillary channel at respective moving speeds corresponding to the properties of the respective hemoglobin molecules, and reach the detecting section provided at the capillary channel.

For example, if the migration liquid included in the capillary channel includes an anionic polymer such as chondroitin sulfate, the anionic polymer flows from the cathode toward the anode. Namely, the anionic polymer moves in the direction opposite to the direction in which the electro-osmotic flow flows. The greater the amount of positive charges the hemoglobin molecular surfaces have, the more easily the hemoglobin molecules are captured by being electrostatically adsorbed by the anionic polymer. Namely, in the capillary channel, the hemoglobin molecules receive force in the direction from the anode to the cathode due to the electro-osmotic flow as described above and force in the direction from the cathode to the anode opposite the electro-osmotic flow due to the anionic polymer. Therefore, the greater the amount of positive charges the hemoglobin molecular surfaces have, the greater force against the electro-osmotic flow the hemoglobin molecules receive, and, thereby, the more slowly the hemoglobin molecules migrate toward the cathode side.

In this way, a speed difference arises between the speed at which a component within the sample is introduced into the capillary channel, and the speed at which the component flows within the capillary channel. Therefore, the concentration of a sample component, at the time when the component within the sample reaches the detecting section of the capillary channel, varies in accordance with this speed difference. Namely, the speed at which a component flows within the capillary channel is slower than the speed at which the component within the sample is introduced into the capillary channel. Therefore, the concentration of a sample component, at the time of reaching the detecting section of the capillary channel, is higher than before being introduced into the capillary channel.

Next, the optical characteristic of a sample component included in the sample liquid arriving at the detecting section is detected, and the amount of change in an optical characteristic value per unit time is derived. Because the sample liquid is fed continuously into the separation flow path, only the components having faster moving speeds are initially measured at the detecting section, but the components having slower moving speeds are gradually added thereto. Therefore, by using an optical characteristic value of a sample component measured at the detecting section, when a graph is drawn with an elapsed time on the horizontal axis and the optical characteristic value on the vertical axis, a curve (e.g., an absorbance curve) increasing monotonically with the passage of time is obtained. In other words, in addition to a same-speed component, which is a sample component of the same moving speed as that of the sample liquid flowing in the separation flow path, a low-speed component, which is a sample component of a slower moving speed than that of the sample liquid and which is introduced to the separation flow path earlier than the same-speed component, and a high-speed component, which is a sample component of a faster moving speed than that of the sample liquid and which is introduced to the separation flow path later than the same-speed component, are also included in the sample liquid reaching the detecting section. Namely, in addition to a sample component having the same moving speed as the sample liquid flowing through the separation flow path, other sample components are also included in the sample liquid arriving at the detecting section. Therefore, since the optical characteristic value is obtained as a value also including those of sample components of different moving speeds flowing through the separation flow path, the optical characteristic value cannot be used as is in separation analysis of sample components.

Thus, the optical characteristic value of the sample liquid flowing through the separation flow path is measured continuously at predetermined time intervals, and the amount of change in the optical characteristic value per unit time is derived. The amount of change in the optical characteristic value per unit time expresses the amount of change in the concentrations of sample components which are included in the sample liquid reaching the detecting section, and which flow through the separation flow path, and whose moving speeds are the same. Therefore, by using the amount of change per unit time in the optical characteristic value, a time distribution of the amount of change in the optical characteristic value per unit time is prepared, and peak areas obtained from the time distribution are determined. Thereby, it is possible to perform separation analysis of sample components flowing through the separation flow path at the same moving speeds. The amount of change in the optical characteristic value per unit time can also be referred to as the value obtained by differentiating the optical characteristic value over time.

A curve having peaks and bottoms (troughs) is drawn as the time distribution of the amount of change in the optical characteristic value per unit time. The peaks are fractions where sample components of the same moving speed through the flow path are collected, and the areas thereof express the integrated values of the amounts of change in the concentrations of the sample components included in the sample liquid reaching the detecting section. In other words, this area is a value in consideration of the concentration ratio due to the speed difference between the speed at which a component within the sample is introduced into the separation flow path, and the speed at which the component flows through the separation flow path. Therefore, this peak area changes when the speed difference between the speed at which the sample liquid flows through the separation flow path, and the speed at which the sample component flows through the separation flow path, and also changes for some reason such as an environmental factor or the like and the proportion at which the sample component has been concentrated changes. Accordingly, accurate separation analysis of sample components is not possible. This problem arises when using a method in which, on the basis of the difference in speeds at which the sample components move within the separation flow path, the sample liquid flows continuously in the separation flow path that separates the sample components, and the sample components are separated and analyzed from the amount of change per unit time in the optical characteristic value of the sample liquid flowing through the separation flow path.

To explain by using capillary electrophoresis as an example, the sample components included in the sample liquid introduced into the capillary channel, flow within the capillary channel at a slower speed than the electro-osmotic flow. On the other hand, the sample liquid flows within the capillary channel as the electro-osmotic flow, and, accompanying this, new sample liquid is continuously supplied into the capillary channel from the exterior of the capillary channel. Therefore, the hemoglobin components included in the sample are concentrated when introduced into the capillary channel, and arrive the measuring section of the capillary channel and are detected at a higher concentration than the concentration thereof at the exterior of the capillary channel. Thus, the amount of change in the optical characteristic value per unit time is obtained as a value in consideration not only of the concentration of a hemoglobin component, but also of the effects on the concentration due to the above-described speed difference between the speed of the electro-osmotic flow and the speed at which the sample component moves within the capillary channel.

The speed of the electro-osmotic flow flowing through the capillary channel, and the moving speeds of the sample components vary due to environmental factors such as pH changes of the migration liquid or the sample liquid due to changes in the environmental temperature, or an increase in the salt concentration in the migration liquid due to storage over a long period of time, or the like. Therefore, the speed difference between the speed at which a sample component is supplied into the capillary channel, and the speed at which the sample component flows through the capillary channel, similarly varies due to such environmental factors. Then, the concentration at the time when a hemoglobin component reaches the measuring section varies, and the amount of change per unit time in the optical characteristic value varies. Thus, the peak area derived from the electropherogram obtained from the amount of change in the optical characteristic value per unit time also fluctuates, and it is not possible to perform accurate separation analysis of the hemoglobin component.

Thus, a correction factor, which represents the proportion or ratio (Vx/V0) of the speed (Vx) at which a sample component flows through the separation flow path with respect to the speed (V0) at which the sample liquid flows through the separation flow path, is derived. Then, the peak area of the fraction including the sample component is derived by being corrected by this correction factor, from the time distribution of the amount of change in the optical characteristic value per unit time which is obtained by detecting the optical characteristic of the sample liquid flowing through the separation flow path. This corrected peak area is an area that excludes the area that fluctuates in accordance with the concentration that arises due to the speed difference between the speed at which the sample liquid flows through the separation flow path and the speed at which the sample component flows through the separation flow path. Therefore, even if the speed difference between the speed at which the sample liquid flows through the separation flow path and the speed at which the sample component flows through the separation flow path changes due to a change in the reagent concentration or an environmental factor such as the environmental temperature or the like, a peak area of the sample component that does not depend on the speed difference can be derived, and accurate separation analysis of the sample component can be carried out on the basis thereof. This correction factor can be refereed to as a reciprocal of the proportion by which a sample component included in the sample liquid is concentrated, due to the speed difference between the speed at which the sample liquid flows through the separation flow path and the speed at which the sample component flows through the separation flow path, at the time when the sample liquid is introduced into the separation flow path.

The corrected peak area may be derived by using the correction factor in a step of deriving the peak area of the fraction including the sample component, from the time distribution of the amount of change in the optical characteristic value per unit time. For example, correction is carried out by multiplying the amount of change in the optical characteristic value per unit time by the correction factor of the sample component corresponding to the amount of change in the optical characteristic value per unit time. Further, a time distribution of the amount of change in the optical characteristic value per unit time may be prepared from the amount of change in the optical characteristic value per unit time which was obtained by the correction, and the peak area of the fraction including the sample component may be derived. Further, as the corrected time distribution of the amount of change in the optical characteristic value per unit time, only the portion from which the peak area is derived may be prepared, or the time distribution may be prepared so as to include portions from which the peak area is not derived.

Further, the time distribution of the amount of change in the optical characteristic value per unit time is prepared from the amount of change in the optical characteristic value per unit time, and the peak area of the fraction including the sample component is derived. Then, the derived peak area of the fraction including the sample component may be corrected by being divided by the correction factor of the sample component. In this case, the peak area may be corrected by deriving the correction factor by using the time when the top of the peak of the fraction is detected, and by considering that the correction factor represents the entire fraction. Further, the peak area may be corrected by deriving respective correction factors by using plural times within the fraction, and by considering that the average correction factor represents the entire fraction.

For the correction factor, the speed (V0) at which the sample liquid flows through the separation flow path and the speed (Vx) at which the sample component flows through the separation flow path may be measured individually, and the proportion (Vx/V0) of the speed (Vx) at which the sample component flows through the separation flow path, with respect to the speed (V0) at which the sample liquid flows through the separation flow path may be derived. The speed at which the sample liquid flows through the separation flow path may be derived by, for example, dividing the amount per unit time of the sample flowing through the separation flow path by a sectional area of the separation flow path. Further, the speed at which the sample component flows through the separation flow path may be derived by, for example, dividing the distance from the introducing port of the sample flow path to the detecting section, by the time period from the point (the first point) in time when the sample liquid is introduced into the sample flow path, to the point (the third point) in time when the sample component is detected by the detecting section provided on the sample flow path.

By the way, providing that Vx is a flowing speed of the sample component, V0 is a flowing speed of the sample liquid, Lx is a distance for which the sample component moves in the separation flow path, L0 is a distance for which the sample fluid moves in the separation path, Tx is a time period during which the sample component moves for Lx and T0 is a time period during which the sample liquid moves for L0, the ratio Vx/V0 is equal to (Lx/Tx)/(L0/T0). Therefore, when Lx is equal to L0, Vx/V0 is equal to T0/Tx. Thus the ratio of the speed can be replaced by the ratio of time.

In a case in which the sample component and the interface between the sample liquid and the flow path liquid filling the separation flow path are detected at the same detecting section, the proportion (T0/Tx) of the time period (T0) from the point in time when introduction of the sample liquid into the separation flow path is started, to the point in time when the detecting section on the sample flow path detects the interface between the sample liquid and the flow path liquid filling the separation flow path, with respect to the time period (Tx) from the point in time when the introduction of the sample liquid into the separation flow path is started, to the point in time when the detecting section detects the sample component, may be made to be the correction factor. The interface between the sample liquid and the flow path liquid filling the separation flow path moves through the separation flow path at the speed at which the sample liquid moves. Then, the distances over which the sample component and the interfaces between the sample liquid and the flow path liquid filling the separation flow path move, are both the distance from the end portion of the separation flow path to the detecting section.

To describe this by using capillary electrophoresis as an example, as described above, when voltage is applied to the both ends of the capillary channel filled with the migration liquid, an electro-osmotic flow is generated toward one of the pair of electrodes (e.g., toward the cathode) within the capillary channel. Then, the migration liquid filling the capillary channel flows toward the one electrode (e.g., the cathode), and the sample liquid contacting the introducing port at the other electrode (e.g., the anode) of the capillary channel is introduced into the capillary channel. Therefore, the correction factor may be derived by using the point in time at which the introduction of the sample liquid into the sample flow path starts, as the point in time at which application of a voltage to the capillary channel is started.

The above-described analysis method serially carries out processes of measurement of the sample, preparation of the electropherogram, derivation of the correction factor and correction of optical measured value in this order. Besides, various ways of correction can be employed as follows. A first possibility is that the correction factor is determined in advance before factory shipment of the analysis device and is stored in a memory of the analysis device, and the stored correction factor is used for correction at a time of measurement of an actual sample. A second possibility is that the correction factor is determined based on an actual sample at a time when the analysis devised is used for the first time. A Third possibility is that the correction factor is determined every time the analysis device is used.

The interface between the sample liquid and the flow path liquid filling the separation flow path may be formed by adding, to the sample liquid, a substance flowing through the separation flow path at the same speed as the speed at which the sample liquid flows through the separation flow path. In other words, the interface may be formed by adding, to the sample liquid, a substance that is not separated even though it flows in the separation flow path. The substance, which is not separated even though it flows in the separation flow path, may be added directly to the sample, or may be added to the sample liquid by the sample liquid being diluted by a dilution liquid to which the substance, which is not separated even though it flows in the separation flow path, has been added. Thereby, between the sample liquid and the flow path liquid, a difference arises in the concentration of the substance that is not separated even though it flows in the separation flow path, and the interface can be formed. Note that a liquid, in which the sample liquid is diluted by a dilution liquid, may be used as the sample liquid.

The interface between the flow path liquid filling the separation flow path and the sample liquid will be described by using capillary electrophoresis as an example. For example, the sample is diluted by a dilution liquid including an inner salt. Thereby, a difference in the concentration of the inner salt arises between the sample liquid diluted by the dilution liquid and the migration liquid filling the capillary channel, and an interface therebetween is formed. Because the inner salt has both positive charges and negative charges within one molecule, in capillary electrophoresis that separates sample components in accordance with the differences in the amounts of charge of the sample components, the inner salt moves through the capillary channel at the same speed as the sample liquid flowing through the capillary channel. Therefore, by detecting the interface formed by the difference in the concentration of the inner salt, the moving speed of the sample liquid flowing through the capillary channel can be measured. The inner salt is preferably a low molecular inner salt. Further, it suffices to form the interface by generating a difference in the concentration of the inner salt at the sample liquid and the migration liquid, and the interface may be formed by using a migration liquid including an inner salt at a concentration sufficiently higher than the sample liquid. Further, 3-(1-pyridino)propanesulfonate is preferably used as the inner salt. The detection of the interface may be the detection of the difference in the refractive indices that arises at the interface, or may be the detection of the inner salt itself.

The optical characteristic is an optical property by which a sample component can be detected. Examples are the light absorption wavelength, the light emission wavelength, and the wavelength of the excitation light of the sample component. The optical characteristic value is the intensity of an optical characteristic value obtained by detecting an optical characteristic, and examples thereof are the absorbance, the light emission intensity, and the fluorescence intensity. The detecting section provided at the separating flow path can be used appropriately in accordance with the optical characteristic to be detected. For example, the detecting section is an absorption spectrometer, a light emission detector, or a fluorescence detector.

The sample liquid in the present invention may be a biological sample such as blood or urine or the like, or may be a sample other than these. Further, the sample liquid may be a liquid from which sample components included in gasses or solids have been extracted. In the present disclosure, in particular, it is preferable that the sample liquid be a biological sample, and it is more preferable that the sample liquid be blood. Further, the sample liquid may be a liquid in which a sample such as blood has been diluted by an appropriate dilution liquid such as a buffering solution or the like. For example, in the case of capillary electrophoresis, it is preferable that the sample be diluted by the migration liquid or by a solution of a composition similar to that of the migration liquid.

Further, it suffices for the sample components in the present invention to be components that can become subjects of analysis. Examples are components having positive charges or negative charges. It is particularly preferable that hemoglobin is the sample component.

Note that the above describes a case in which the speed at which a sample component flows through the capillary channel is slower than the speed at which the sample component is supplied into the flow path. However, the present invention can be implemented similarly also in cases in which the speed at which the sample component flows within the flow path is faster than the speed at which the sample component is supplied into the flow path. Namely, if the speed at which the sample component flows within the flow path is faster than the speed at which the sample component is supplied into the flow path, the sample component reaches and is detected at the detecting region of the capillary channel at a concentration lower than the concentration thereof at the exterior of the capillary channel. Therefore, the amount of change in the optical characteristic value per unit time is obtained as a value in consideration not only of the concentration of the sample component, but also of the effects of dilution due to the above-described difference in speeds. Namely, the amount of change in the optical characteristic value per unit time is obtained as a value lower than the value expressed by the concentration of the sample component. Thus, by similarly correcting the amount of change in the signal strength per unit time by using the above-described correction factor, the respective components can be separated and analyzed correctly.

Embodiments of the present disclosure are described hereinafter with reference to the drawings. Note that, although capillary electrophoresis is described as an example, as described above, the present invention is not limited to capillary electrophoresis.

[Analyzing System]

FIG. 1 shows a schematic configuration of an example of an analyzing system A1 by which a method of measuring stable hemoglobin A1c of the present disclosure is implemented. The analyzing system A1 is configured to have an analyzing device 1 and an analysis chip 2. The analyzing system A1 is a system that carries out separation analysis, which is based on the principles of cation exchange, on the basis of the molecular surface charges of hemoglobin by using blood sample Sa, which is blood collected from a human body, as the subject.

<Preparation of Analysis Chip>

Figure 2:
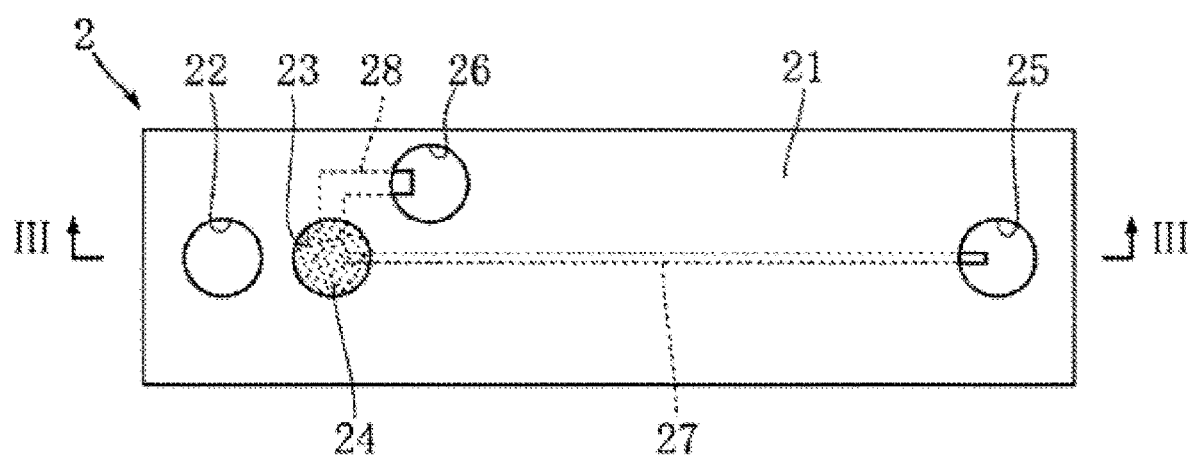
FIG. 2 is a plan view showing an exemplary analysis chip used in the analyzing system of FIG. 1.
Figure 3:
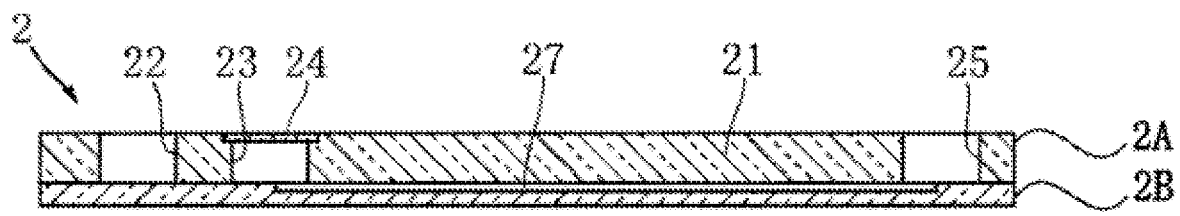
FIG. 3 is a cross-sectional view along line of FIG. 2.

The analysis chip 2 retains the blood sample Sa, and, in a state of being loaded in the analyzing device 1, provides a place for the analysis of the blood sample Sa as an analysis subject. In the present embodiment, the analysis chip 2 is configured as a so-called disposable analysis chip intended to be disposed of after completion of one-time analysis. As shown in FIG. 2 and FIG. 3, the analysis chip 2 has a main body 21, a mixing reservoir 22, an introducing reservoir 23, a filter 24, a discharge reservoir 25, an electrode reservoir 26, a capillary channel 27, and a connecting flow path 28. FIG. 2 is a plan view of the analysis chip 2, and FIG. 3 is a cross-sectional view along line III-III of FIG. 2. Note that the analysis chip 2 is not limited to a disposable type chip, and may be a chip that can be used over plural analyses. Further, the analyzing system of the present embodiment is not limited to a configuration in which the analysis chip 2 that is a separate body is loaded into the analyzing device 1, and may be a configuration in which a functional region, which exhibits a function similar to that of the analysis chip 2, is incorporated into the analyzing device 1.

The main body 21 is a base of the analysis chip 2. The material thereof is not particularly limited, and glass, fused silica, plastic and the like are examples thereof. In the present embodiment, the main body 21 has a configuration in which an upper side portion 2A and a lower side portion 2B in FIG. 3 are formed as separate bodies, and are joined together. Note that the present disclosure is not limited to this, and, for example, the main body 21 may be formed integrally.

The mixing reservoir 22 is an example of the place at which a mixing step, which is described later and in which the blood sample Sa and a dilution liquid Ld are mixed, is carried out. The mixing reservoir 22 is configured, for example, as a concave portion that opens upwardly by a through-hole formed in the upper side portion 2A of the main body 21. The introducing reservoir 23 is a reservoir into which is introduced a sample liquid Sm as a specimen solution and is obtained by the mixing step in the mixing reservoir 22. The introducing reservoir 23 is configured, for example, as a concave portion that opens upwardly by a through-hole formed in the upper side portion 2A of the main body 21.

The filter 24 is provided at the opening portion of the introducing reservoir 23 that is an example of the path of introduction into the introducing reservoir 23. The exact configuration of the filter 24 is not limited, and, for example, a cellulose acetate film filter (manufactured by Advantec, and having a hole diameter of 0.45 μm) is a suitable example.

The discharge reservoir 25 is a reservoir positioned at a downstream side of the electro-osmotic flow in the electrophoresis. The discharge reservoir 25 is configured, for example, as a concave portion that opens upwardly by a through-hole formed in the upper side portion 2A of the main body 21. The electrode reservoir 26 is a reservoir into which an anode 31 is inserted in the analysis step in electrophoresis. The electrode reservoir 26 is configured, for example, as a concave portion that opens upwardly by a through-hole formed in the upper side portion 2A of the main body 21. The connecting flow path 28 connects the introducing reservoir 23 and the electrode reservoir 26, and provides a conduction path between the introducing reservoir 23 and the electrode reservoir 26.

The capillary channel 27 is a minute flow path that connects the introducing reservoir 23 and the discharge reservoir 25, and is the place at which the electro-osmotic flow (EOF) in the electrophoresis arises. The capillary channel 27 is, for example, configured as a groove formed in the lower side portion 2B. Note that concave portions or the like, which are for promoting the illumination of light onto the capillary channel 27 and the exiting of light transmitted through the capillary channel 27, may be formed appropriately in the main body 21. The size of the capillary channel 27 is not particularly limited, but, as an example, the width thereof is 25 μm to 100 μm, and the depth thereof is 25 μm to 100 μm, and the length thereof is 5 mm to 150 mm. The whole size of the analysis chip 2 is appropriately designed in accordance with the size of the capillary channel 27, and sizes and an arrangement of the mixing reservoir 22, the introducing reservoir 23, the discharge reservoir 25 and the electrode reservoir 26, and the like.

Note that the analysis chip 2 of the above-described configuration is an example, and any analysis chip of a configuration that is such that analysis by electrophoresis is possible can be suitably employed.

<Analyzing Device>

The analyzing device 1 carries out analyzing processing with the blood sample Sa as the analysis subject, in a state in which the analysis chip 2 on which the blood sample Sa is dripped is loaded therein. As shown in FIG. 1, the analyzing device 1 has the anode 31, a cathode 32, a light source 41, an optical filter 42, a lens 43, a slit 44, a detector 5, a dispenser 6, a pump 61, a dilution liquid reservoir 71, a migration liquid reservoir 72 and a control section 8. Note that the light source 41, the optical filter 42, the lens 43 and the detector 5 configure an example of a measuring section in the present disclosure.

The anode 31 and the cathode 32 are a pair of electrodes for applying a predetermined voltage to the capillary channel 27 in the electrophoresis step. The anode 31 is inserted in the electrode reservoir 26 of the analysis chip 2, and the cathode 32 is inserted in the discharge reservoir 25 of the analysis chip 2. The voltage applied between the anode 31 and the cathode 32 is not particularly limited, and is, for example, 0.5 kV to 20 kV.

The light source 41 is a region that emits light for measuring the absorbance as an optical measured value in the electrophoresis. The light source 41 has, for example, an LED chip that emits light of a predetermined wavelength range. The optical filter 42 attenuates light of a predetermined wavelength of the light from the light source 41, and transmits light of other wavelengths. The lens 43 focuses the light transmitted through the optical filter 42 onto a place of analysis at the capillary channel 27 of the analysis chip 2. The slit 44 is for removing excess light that potentially gives rise to scattering or the like, among the light focused by the lens 43.

The detector 5 receives the light, from the light source 41 transmitted through the capillary channel 27 of the analysis chip 2, and is configured so as to have, for example, photodiodes or a photo IC or the like.

In this way, a path by which the light emitted from the light source 41 reaches the detector 5 is an optical path. Further, the optical measured value of the solution (i.e., either the specimen solution or the migration liquid, or a mixed solution thereof) flowing through the capillary channel 27 is measured at the position where this optical path intersects the capillary channel 27. Namely, the position of the capillary channel 27 intersected by the optical path from the light source 41 to the detector 5 is the measuring section of the optical measured value. Absorbance is an example of the optical measured value. Absorbance expresses a proportion of the light of the optical path absorbed by the solution flowing through the capillary channel 27, and is expressed as an absolute value of a common logarithm value of a ratio of an incident light intensity and a transmitted light intensity. In this case, a general-purpose spectrophotometer can be used as the detector 5. Note that absorbance does not have to be used, and any value provided that it is an optical measured value, such as simply the value of the transmitted light intensity itself or the like, can be used in the present invention. Hereinafter, a case in which absorbance is used as the optical measured value is described as an example.

The dispenser 6 dispenses predetermined amounts of the dilution liquid Ld or the migration liquid Lm and the sample liquid Sm, and includes a nozzle for example. The dispenser 6 can be freely moved to plural positions within the analyzing device 1 by an unillustrated driving mechanism. The pump 61 is a suction source and a discharge source with respect to the dispenser 6. The pump 61 may be used as a suction source and a discharge source of unillustrated ports provided at the analyzing device 1. These ports are used to fill the migration liquid Lm and the like. Further, a pump for exclusive use separate from the pump 61 may be provided.

The dilution liquid reservoir 71 is a reservoir for storing the dilution liquid Ld. The dilution liquid reservoir 71 may be a reservoir provided permanently at the analyzing device 1, or, a container in which a predetermined amount of the dilution liquid Ld is sealed may be loaded into the analyzing device 1. The migration liquid reservoir 72 is a reservoir for storing the migration liquid Lm. The migration liquid reservoir 72 may be a reservoir provided permanently at the analyzing device 1, or, a container in which a predetermined amount of the migration liquid Lm is sealed may be loaded into the analyzing device 1.

Figure 4:
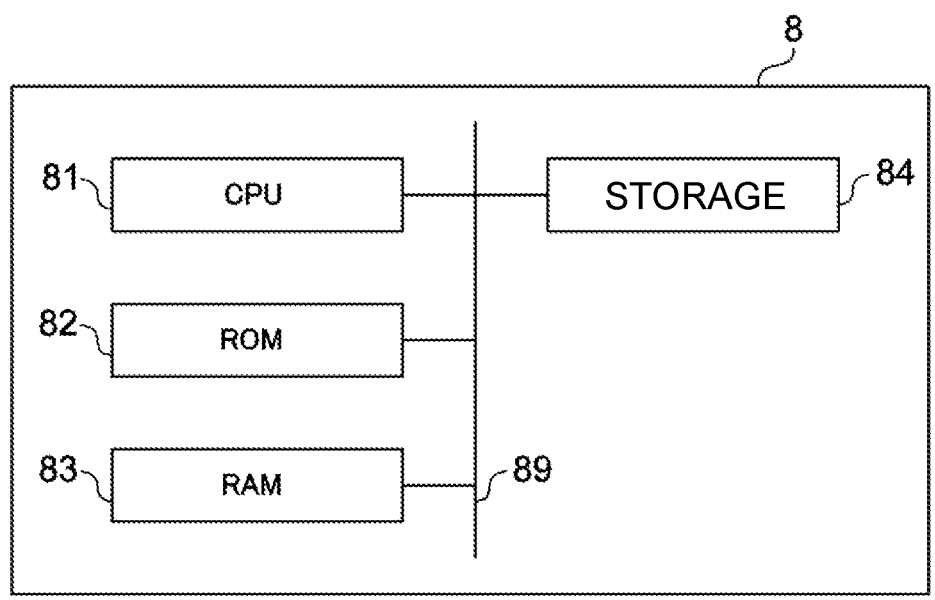
FIG. 4 is a block drawing showing a hardware configuration of a control section.

The control section 8 controls respective sections in the analyzing device 1. As shown by a hardware configuration in FIG. 4, the control section 8 has a CPU (Central Processing Unit) 81, a ROM (Read Only Memory) 82, a RAM (Random Access Memory) 83, and a storage 84. The respective configurations are connected via a bus 89 so as to be able to communicate with one another.

The CPU 81 is the central computing processing unit, and executes various types of programs and controls the respective sections. Namely, the CPU 81 reads a program out from the ROM 82 or the storage 84, and executes the program by using the RAM 83 as a workspace. The CPU 81 controls the above-described respective configurations and carries out various types of computing processings, in accordance with the programs recorded in the ROM 82 or the storage 84.

The ROM 82 stores various types of programs and various types of data. The RAM 83 temporarily stores programs and data as a workspace. The storage 84 is configured by an HDD (Hard Disk Drive), an SSD (Solid State Drive) or a flash memory, and stores various types of programs, including the operating system, and various types of data. In the present aspect, the programs and the various data that relate to measurement and judgment are stored in the ROM 82 or the storage 84. Further, measured data can be stored in the storage 84 as well.

Figure 5:
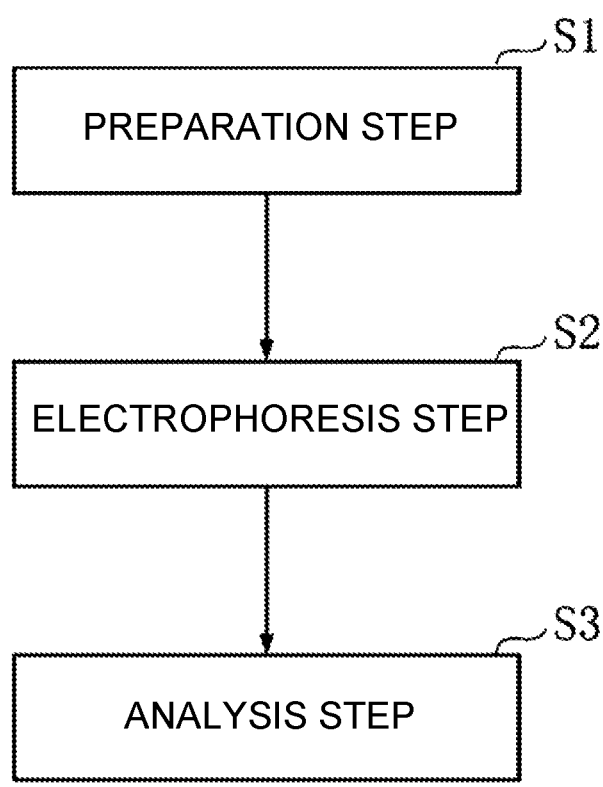
FIG. 5 is a flowchart showing an analyzing method according to an embodiment of the present invention.

The control section 8 executes respective steps shown in FIG. 5 at the analyzing device 1 by the CPU 81, among the above-described hardware configuration, executing the aforementioned programs. Details of these steps are described later.

<Preparation of Dilution Liquid, Migration Liquid and Sample Liquid>

The dilution liquid Ld, by being mixed with the blood sample Sa, generates the sample liquid Sm as the specimen solution. A main agent of the dilution liquid Ld is not particularly limited, and water and saline are examples thereof, and liquids of components similar to those of the migration liquid Lm described hereinafter are preferable examples thereof. Further, in addition to the aforementioned main agent, additives may be added as needed to the dilution liquid Ld. In the present embodiment, 1-(3-sulfopropyl) pyridinium hydroxide inner salt is added to the dilution liquid Ld as the additive. The inner salt is added in order to give rise to a difference in concentrations in the sample liquid Ld and the migration liquid Lm. The inner salt moves within the capillary channel 27 by the flow of the electro-osmotic flow and without being affected by electrostatic force. Therefore, the time period until the interface between the sample liquid Sm and the migration liquid Lm, which is generated by the difference in the concentration of the inner salt, is a standard for a speed of the electro-osmotic flow.

Note that it suffices for the additives to be substances that are not affected by the migration speed other than by the flow of the liquid within the capillary channel 27, and in addition to the aforementioned inner salt, additives can be selected appropriately in accordance with the method of separation within the capillary channel 27. However, because separation is carried out by capillary electrophoresis, a substance that does not have low molecular charges is preferable. Further, because it suffices for a difference in the concentration of the substance to arise between the sample liquid Sm and the migration liquid Lm, the dilution liquid Ld may include this component, or the migration liquid Lm may include this component. Moreover, both the dilution liquid Ld and the migration liquid Lm may include this component provided that such a difference in concentration will arise.

The other compositions included in the dilution liquid Ld also can be selected appropriately in accordance with the separation method.

The migration liquid Lm is a medium filled into the discharge reservoir 25 and the capillary channel 27 in the step of analyzing in accordance with electrophoresis, and generates the electro-osmotic flow in the electrophoresis. The migration liquid Lm is not particularly limited, but a liquid that employs an acid is desirable. The acid is, for example, citric acid, maleic acid, tartaric acid, succinic acid, fumaric acid, phthalic acid, malonic acid, or malic acid. Further, it is preferable that the migration liquid Lm include a weak base. Examples of the weak base are arginine, lysine, histidine, tris and the like. The pH of the migration liquid Lm is in the range of a pH of 4.5 to 6 for example. MES, ADA, ACES, BES, MOPS, TES, HEPES and the like are types of buffers of the migration liquid Lm. Further, in the same way as mentioned in the description of the dilution liquid Ld, additives may be added to the migration liquid Lm as needed. In the present embodiment, chondroitin sulfate is added to the migration liquid Lm as an additive. Chondroitin sulfate is added for the purpose of covering an inner wall of the capillary channel 27 with an anionic polymer, and, in addition, for the purpose of imparting a difference in the migration speeds in accordance with the amount of the positive charges by binding with the positive charges of the hemoglobin molecular surfaces.

The other compositions included in the migration liquid Lm also can be selected appropriately in accordance with the separation method.

Note that the migration liquid Lm and the dilution liquid Ld can be selected arbitrarily provided that they are a combination such that a change in the optical measured value, which results from the arrival of the interface between the migration liquid Lm and the sample liquid Sm in which the blood sample is diluted by the dilution liquid Ld, arises at the interface detection point in time as described later.

An example of the analyzing method relating to the present invention, which is carried out by using the analyzing system A1, is described hereinafter. FIG. 5 is a flowchart showing the analyzing method of the present embodiment. The present analyzing method has a preparation step S1, an electrophoresis step S2, and an analysis step S3.

<Preparation Step S1>

Figure 6:
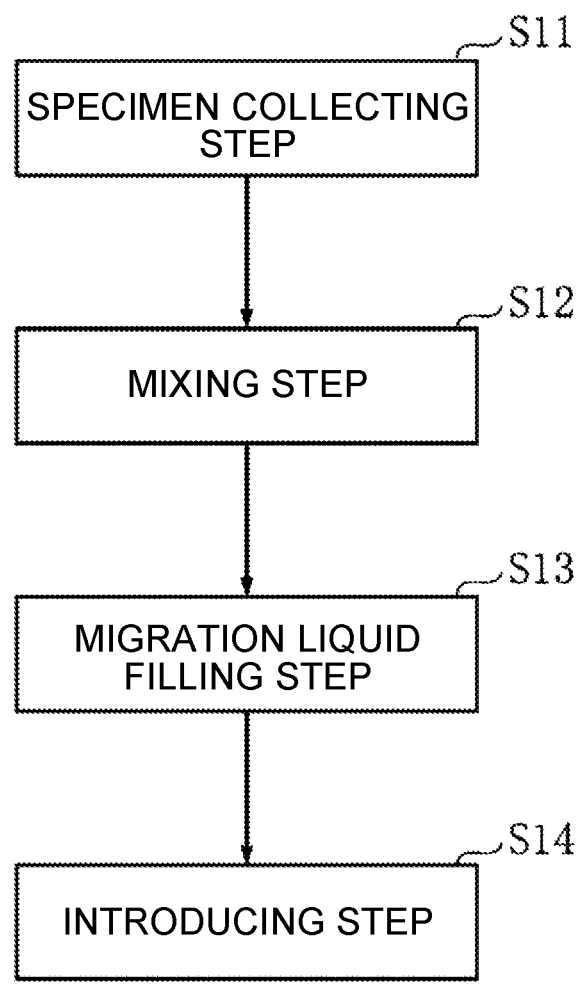
FIG. 6 is a flowchart showing the processes of a preparation step.

FIG. 6 is a flowchart showing the processes of the preparation step S1. In the present embodiment, as shown in FIG. 6, the preparation step S1 has a specimen collecting step S11, a mixing step S12, a migration liquid filling step S13, and an introducing step S14.

<Specimen Collecting Step S11>

First, the blood sample Sa is readied. In the present embodiment, the blood sample Sa is blood collected from a human body. The blood may be whole blood, component-separated blood, or hemolyzed blood, or the like. Then, the analysis chip 2, onto which the blood sample Sa has been dispensed, is loaded into the analyzing device 1.

<Mixing Step S12>

Figure 7:
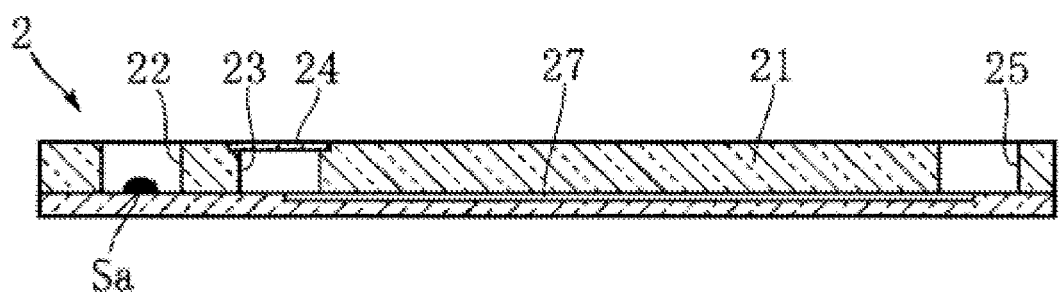
FIG. 7 is a cross-sectional view showing a step of the preparation step of FIG. 6.
Figure 8:
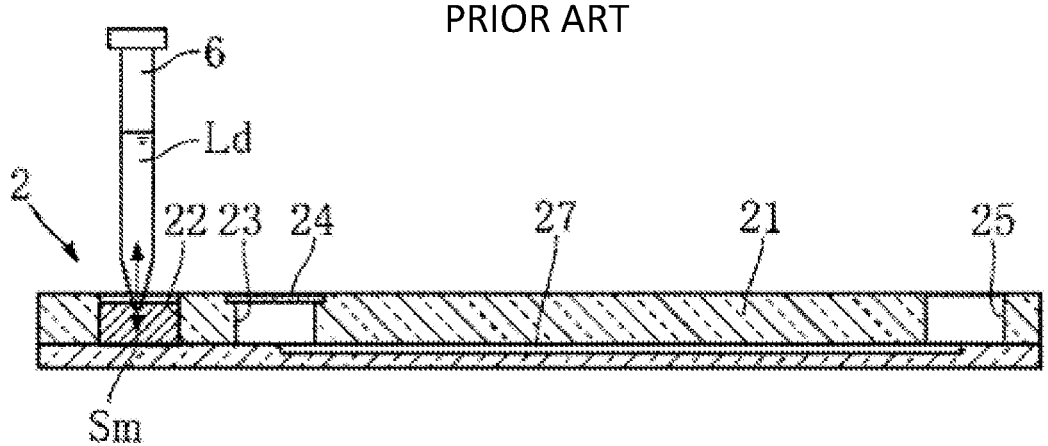
FIG. 8 is a cross-sectional view showing a step of the preparation step of FIG. 6.

Next, the blood sample Sa and the dilution liquid Ld are mixed together. As shown in FIG. 7, a predetermined amount of the blood sample Sa is dripped into the mixing reservoir 22 of the analysis chip 2. Next, a predetermined amount of the dilution liquid Ld of the dilution liquid reservoir 71 is aspirated by the dispenser 6, and, as shown in FIG. 8, the predetermined amount of the dilution liquid Ld is dispensed into the mixing reservoir 22 of the analysis chip 2. Then, by using the pump 61 as the suction source and the discharge source, aspiration and discharge of the dilution liquid Ld from the dispenser 6 is repeated. Thereby, the blood sample Sa and the dilution liquid Ld are mixed-together at the mixing reservoir 22, and the sample liquid Sm as a specimen solution is obtained. The mixing of the blood sample Sa and the dilution liquid Ld may be carried out by a method other than aspiration and discharge by the dispenser 6.

<Migration Liquid Filling Step S13>

Figure 9:
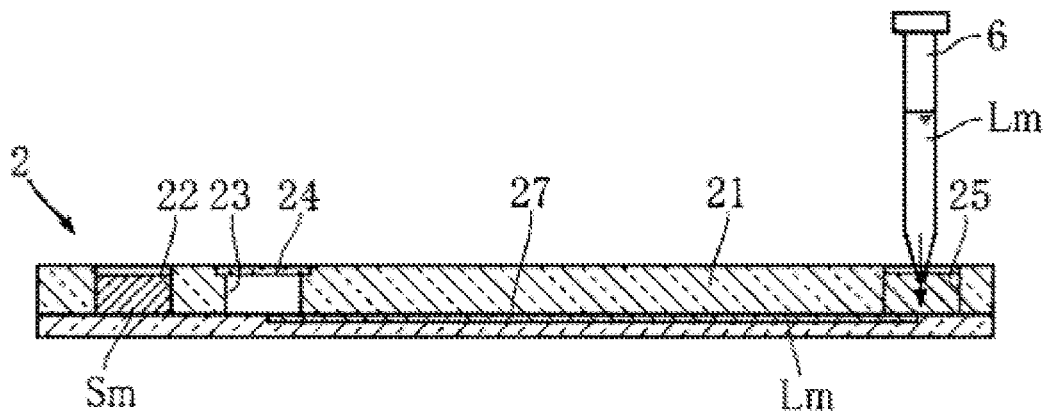
FIG. 9 is a cross-sectional view showing a step of the preparation step of FIG. 6.

Next, a predetermined amount of the migration liquid Lm of the migration liquid reservoir 72 is aspirated by the dispenser 6, and, as shown in FIG. 9, the predetermined amount of the migration liquid Lm is dispensed into the discharge reservoir 25 of the analysis chip 2. Then, the opening at the upper side of the discharge reservoir 25 is covered by the aforementioned port, and the discharge reservoir 25 and the capillary channel 27 is filled with the migration liquid Lm by a method such as appropriately discharging and aspirating air with respect to the discharge reservoir 25 interior from the port, or the like.

<Introducing Step S14>

Figure 10:
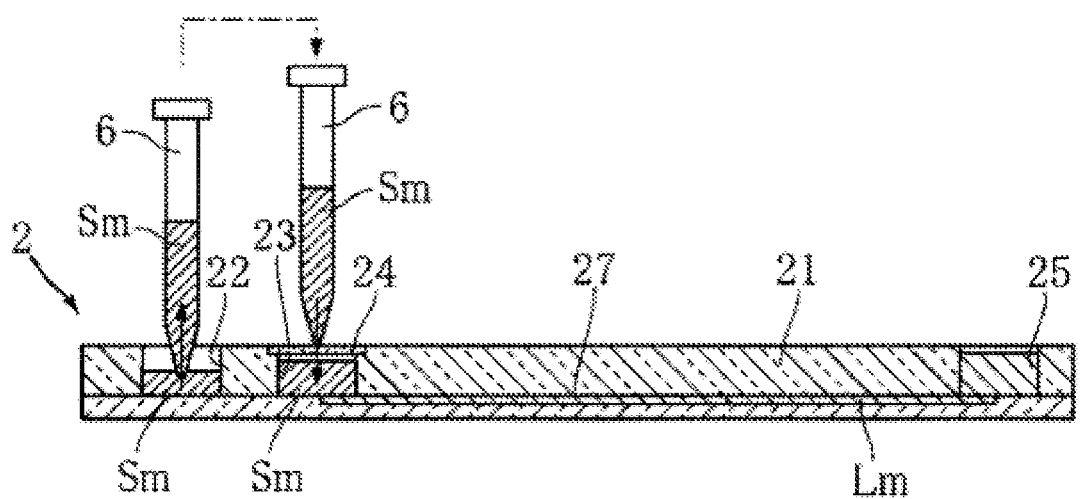
FIG. 10 is a cross-sectional view showing a step of the preparation step of FIG. 6.

Next, as shown in FIG. 10, a predetermined amount of the sample liquid Sm is collected from the mixing reservoir 22 by the dispenser 6. Then, the predetermined amount of the sample liquid Sm is introduced into the introducing reservoir 23 from the dispenser 6. In this introduction, the sample liquid Sm passes through the filter 24 provided at the opening portion of the introducing reservoir 23 that is an example of the path of introduction into the introducing reservoir 23. Further, in the present embodiment, the sample liquid Sm is filled from the introducing reservoir 23 through the connecting flow path 28 into the electrode reservoir 26. At this time, flowing of the sample liquid Sm from the introducing reservoir 23 via the connecting flow path 28 to the electrode reservoir 26 occurs. However, from the introducing reservoir 23 to the connecting flow path 28, the sample liquid Sm flows in a direction substantially orthogonal to the length direction of the capillary channel 27 (see FIG. 2). On the other hand, the migration liquid Lm of the capillary channel 27 hardly moves at all at this stage. As a result, due to shear flow arising at the connecting portion of the introducing reservoir 23 and the capillary channel 27 (see FIG. 3), there occurs a state in which a distinct interface arises between the sample liquid Sm and the migration liquid Lm. Note that, provided that it is a method by which an interface arises between the sample liquid Sm and the migration liquid Lm, any means can be employed such as physically providing a movable filter at the border between the introducing reservoir 23 and the capillary channel 27, or changing the method of flowing by control, or the like.

<Electrophoresis Step S2>

Next, the anode 31 is inserted in the electrode reservoir 26 (see FIG. 2), and the cathode 32 is inserted in the discharge reservoir 25 (see FIG. 1). Subsequently, voltage is applied to the anode 31 and the cathode 32 in accordance with an instruction from the control section 8. This voltage is, for example, 0.5 kV to 20 kV. Thereby, an electro-osmotic flow is generated, and the sample liquid Sm is gradually moved within the capillary channel 27 from the introducing reservoir 23 to the discharge reservoir 25. At this time, because the sample liquid Sm is filled in the introducing reservoir 23, hemoglobin (Hb) as the above-described analysis component is electrophoresed in a state in which the sample liquid Sm is being continuously supplied at the capillary channel 27. At this time, the sample liquid Sm migrates through the capillary channel 27 while pushing the migration liquid Lm in a downstream direction, while the state in which the above-described interface is maintained between the sample liquid Sm and the migration liquid Lm remains as is. Then, emission of light from the light source 41 is started, and measurement of the absorbance by the detector 5 is carried out. Then, the relationship between absorbance and the time elapsed from the start of application of a voltage to the anode 31 and the cathode 32 is measured.

At this time, at the introducing reservoir 23 and the capillary channel 27, the hemoglobin receives force by the electro-osmotic flow to move toward the cathode 32, and force by the electrostatic force of the hemoglobin to move toward the cathode 32 side, and force to be pushed back toward the anode 31 side due to binding with the chondroitin sulfate.

Here, the sectional area of the introducing reservoir 23, which is perpendicular to the migration direction, is much larger than the sectional area of the capillary channel 27. Therefore, there is hardly any electric potential difference within the introducing reservoir 23, and the force by the electrostatic force to move toward the cathode 32 side, and the force to be pushed back toward the anode 31 side due binding with the chondroitin sulfate, hardly work at all. Thus, the hemoglobin receives the force by the electro-osmotic flow, and is introduced into the capillary channel 27.

On the other hand, the sectional area of the capillary channel 27 is extremely small as compared with the sectional area of the introducing reservoir 23, which is perpendicular to the migration direction. Therefore, the electric potential difference within the capillary channel 27 is larger than the electric potential difference within the introducing reservoir 23. Thus, at the capillary channel 27, the hemoglobin receives the force by the electro-osmotic flow to move toward the cathode 32 side, and the force by the electrostatic force to move toward the cathode 32 side, and the force to be pushed back toward the anode 31 due to the binding with the chondroitin sulfate. However, the electrostatic force that results from the positive charges of the hemoglobin is very much smaller than the force imparted by the electro-osmotic flow and the force to be pushed back toward the anode 31 side by binding with the chondroitin sulfate, and thus can be ignored. Further, the force imparted by the electro-osmotic flow is larger than the force to be pushed back toward the anode 31 side by binding with the chondroitin sulfate. Therefore, in the capillary channel 27, the hemoglobin receives a total force imparted of the force by the electro-osmotic flow subtracted by the force to be pushed back toward the anode 31 side due to binding with the chondroitin sulfate, and the hemoglobin moves from the anode 31 side to the cathode 32 side. Namely, the hemoglobin is supplied to the capillary channel 27 at the speed of the electro-osmotic flow, but migrates within the capillary channel 27 at a speed slower than the electro-osmotic flow. The force to be pushed back toward the anode 31 side due to the binding with the chondroitin sulfate, differs in accordance with the type of the hemoglobin. The greater amount of positive charges the molecular surface has, the more the molecule binds with the chondroitin sulfate, and, therefore, the greater the force by which the hemoglobin is pushed back toward the anode 31 side. Accordingly, the greater the amount of the positive charges the molecular surface of the hemoglobin has, the slower the moving speed of the hemoglobin within the capillary flow path, and, thereby, the respective components of the hemoglobin are separated. On the other hand, the speed of the electro-osmotic flow, into which the hemoglobin included in the sample liquid Sm is supplied into the capillary channel 27, is faster than the speed at which the hemoglobin moves within the capillary channel 27, and a difference in speeds arises. Therefore, the hemoglobin is concentrated at the sample liquid introducing port of the capillary channel 27. Further, the greater amount of the positive charges the molecular surface of the hemoglobin has, the greater the aforementioned difference in speeds becomes, and, therefore, the concentration grows greater.

<Analysis Step S3>

Figure 11:
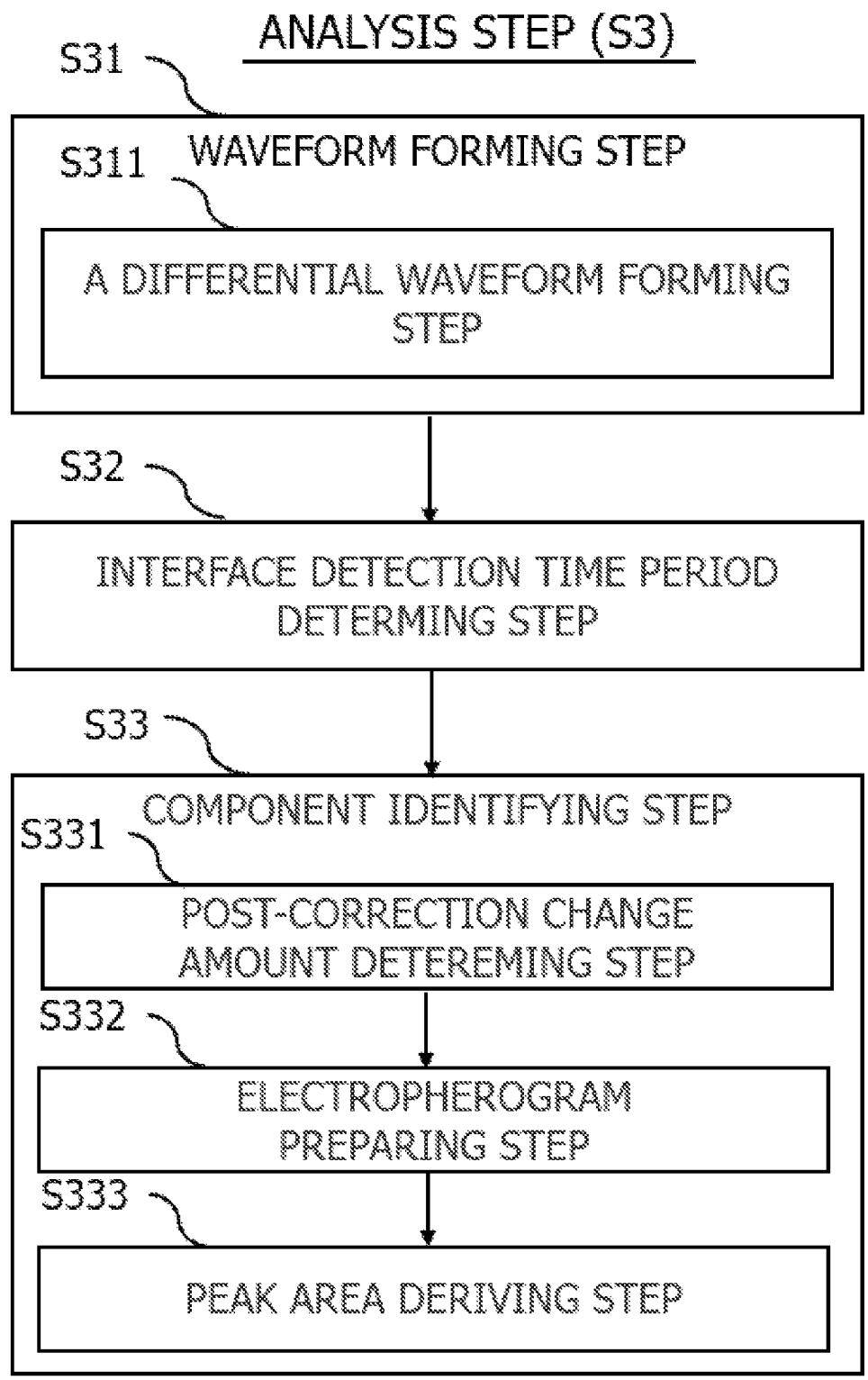
FIG. 11 is a flowchart showing processes of an analysis step.

Here, the absorbance peak, which corresponds to a component having a relatively fast moving speed within the sample liquid Sm, appears at a point (the third point) in time when the elapsed time from the aforementioned start of application of the voltage (the first point) is relatively short. On the other hand, the absorbance peak, which corresponds to a component having a relatively slow moving speed within the sample liquid Sm, appears at a point (the third point) in time when the elapsed time from the aforementioned start of application of the voltage (the first point) is relatively long. Analysis (separation and measurement) of the components within the sample liquid Sm is carried out by utilizing this. The analysis step S3 shown in FIG. 11 is executed by control of the control section 8 and on the basis of the measured absorbance. The analysis step S3 of the present embodiment includes a waveform forming step S31, an interface detection time period determining step S32, and a component identifying step S33.

<Waveform Forming Step S31>

Figure 12:
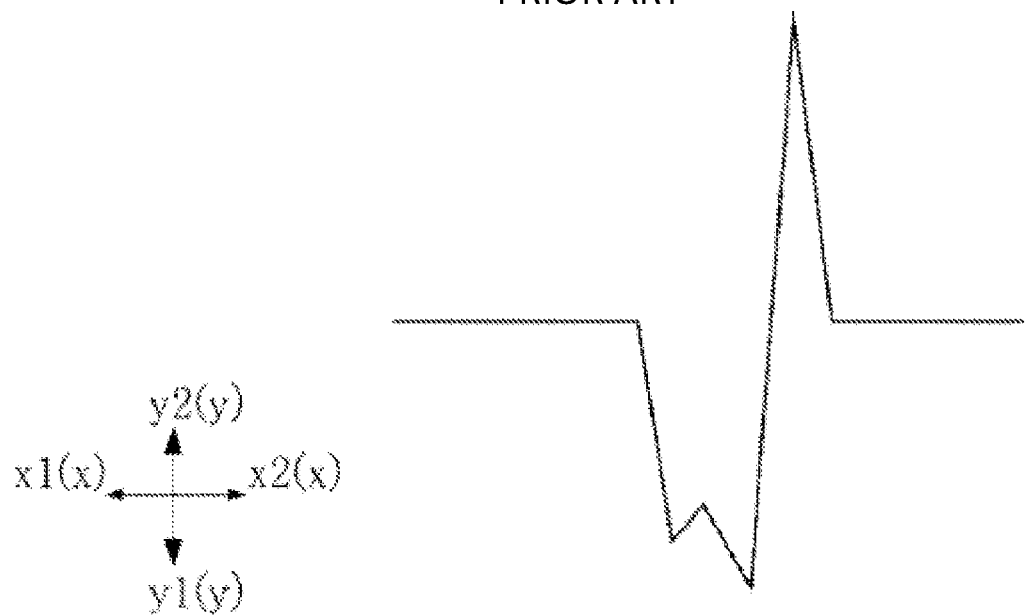
FIG. 12 is a graph showing an example of waveform data formed by a waveform forming step.

In the present step, an electropherogram is prepared by the control section 8 carrying out computing processing on the measured absorbance. Here, the voltage application start time is used as the measurement start time, and an electropherogram as a measured waveform expressing the change in the absorbance which is the optical measured value corresponding to the time elapsed from after the aforementioned start of measurement, is formed. The waveform forming step S31 of the present embodiment includes a differential waveform forming step S311. The differential waveform forming step S311 forms a waveform of the differential values by differentiating the measured absorbance with respect to time. FIG. 12 shows an example of a differential waveform formed by the differential waveform forming step S311. The x-axis in the drawing is a time axis, and the y-axis is a differential value axis. In the following drawings and explanation, the negative direction side along the time axis x is direction x1 side, and the positive direction side is direction x2 side. The negative direction side along the differential value axis y is direction y1 side, and the positive direction side is direction y2 side.

<Interface Detection Time Period Determining Step S32>

Figure 13:
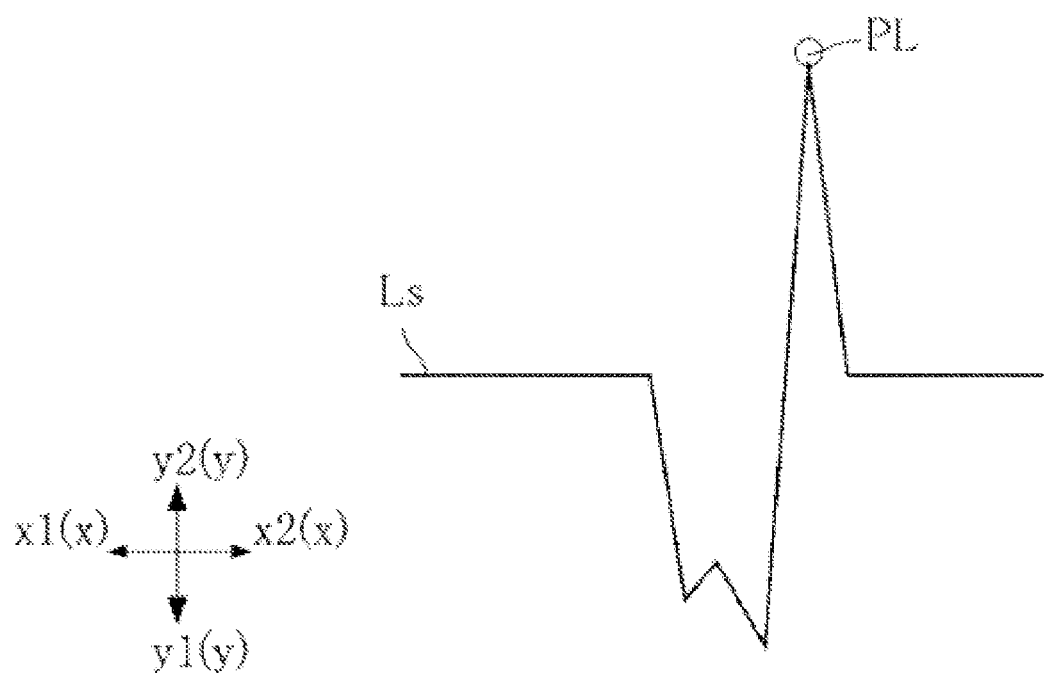
FIG. 13 is a graph showing the determination of a furthest point.

The present step is a step of determining the interface arrival point in time which is the point in time at which the interface between the mixed specimen Sm and the migration liquid Lm migrating in the downstream direction of the capillary channel due to the application of the voltage, arrives at the detector 5. The interface between the mixed specimen Sm and the migration liquid Lm is a peak appearing first after the start of electrophoresis. The peak of the interface of the mixed specimen Sm and the migration liquid Lm is shown in FIG. 13. Next, as shown in FIG. 13, of the peak shown by the interface of the mixed specimen Sm and the migration liquid Lm, the point, at which the differential value is furthest away from a reference value Ls in the electropherogram, is determined. In the illustrated example, the point apart from the reference value Ls in direction y2 is the furthest apart from the reference value Ls, and this point is determined as furthest point PL. Here, the point in time at which the application of the voltage starts in the above-described electrophoresis step S2 is 0, and the point in time when this furthest point PL is detected is the interface detection point in time, and the elapsed time from the start of the electrophoresis (the first point) to the interface detection point (the second point) in time is the interface detection time period. pC<omponent Identifying Step S33>

Figure 14:
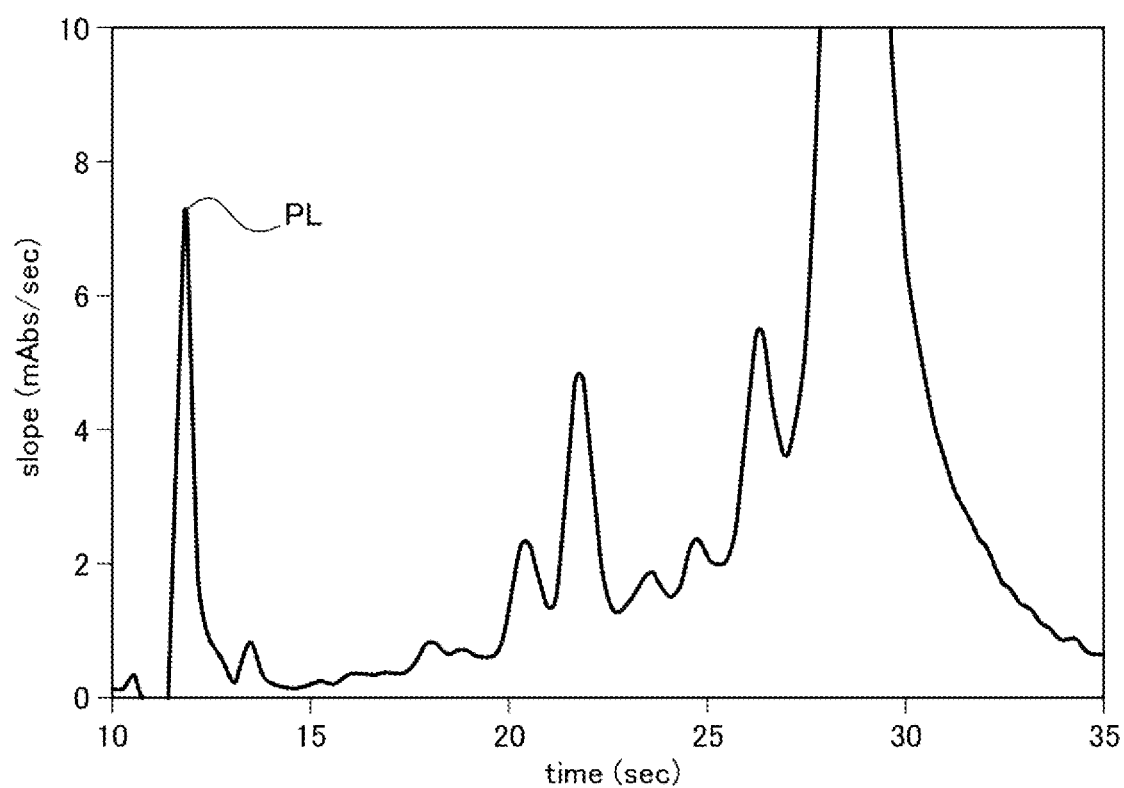
FIG. 14 is an example of a differential waveform from an interface detection point in time and thereafter.

An example of the differential waveform after the interface detection point in time, which is obtained in the above-described waveform forming step S31, is shown in FIG. 14. In this drawing, the x-axis shows the migration time period (unit: sec) with the point in time at which application of the voltage is started being 0, and the y-axis shows the slope value (unit: mAbs/sec) that is the value obtained by differentiating the absorbance with respect to time. Namely, this slope value is the value of the slope of the absorbance curve at each point in time, which gradually increases monotonically as time passes and is the amount of change per unit time in the optical characteristic value of each elapsed time period. Further, the peak in the vicinity of a migration time of 11.5 seconds is the furthest point PL shown in FIG. 13, and the elapsed time period at the point in time when this furthest point PL appears is the interface detection time period determined in the above-described interface detection time period determining step. The peak expressed by this PL shows the point in time when, in actuality, the 1-(3-sulfopropyl)pyridinium hydroxide inner salt is initially detected. This 1-(3-sulfopropyl)pyridinium hydroxide inner salt does not bind with the chondroitin sulfate, and flows within the flow path in the direction from the anode toward the cathode at the speed of the electro-osmotic flow. Namely, the speed at the time when the inner salt is introduced into the capillary channel 27, and the speed at which the inner salt flows through the capillary channel 27, are both the speed of the electro-osmotic flow, and there is no speed difference therebetween. Therefore, the leading edge of the sample liquid can be detected by detecting the inner salt. In the component identifying step S33, by using this interface detection time period as a reference, a correction factor of the slope value at each elapsed time period is derived, and the amount of change per unit time in the corrected optical characteristic value is determined, and the peak area of the fraction including the hemoglobin component is derived on the basis of the electropherogram created thereby.

As described above, the greater amount of positive charges the hemoglobin molecular surfaces have, the higher the concentration grows. Accordingly, for example, the later the elapsed time of the hemoglobin is, the greater the component amount of the sample component measured from the area of the differential waveform shown in FIG. 14 becomes. Namely, if there are sample components having the same component amounts, the sample component, whose speed of flowing through the flow path is slow, is measured as having a greater component amount than the component whose speed of flowing through the flow path is fast.

On the other hand, when a change in the reagent concentration, or a change in the concentration or the environmental temperature, arises during storage of the dilution liquid Ld and the migration liquid Lm, the speed of the electroosmotic flow and the moving speed of the chondroitin sulfate change. Therefore, the difference in the moving speeds before and after the various hemoglobin components are introduced into the capillary channel 27 also changes, and the concentration rate also changes. Thereby, even if the same blood sample is measured, the amount of change in the absorbance per unit time (i.e., the slope value as the amount of change in the optical characteristic value per unit time) changes due to effects of storage and effects of the environmental temperature. As a result, the peak area of a predetermined hemoglobin component (e.g., HbA1c), which is derived by using the results of measurement of the absorbance per unit time, also changes, and the ratio of the predetermined hemoglobin component with respect to the total hemoglobin also changes. Accordingly, if the value of this predetermined hemoglobin component is derived on the basis of a calibration curve created by using a standard sample, the values of even the same blood samples will vary due to the measuring conditions and the measuring environment, and a correct value cannot be measured.

In this way, correction for making the value approach a value expressing the actual amount of the hemoglobin component is carried out as follows, without the amount of change per unit time in the optical characteristic value subjected to concentration due to the moving speed of the hemoglobin component within the capillary channel 27, or the amount of change per unit time in the optical characteristic value subjected to fluctuation due to the measuring conditions and the measuring environment, depending on the concentration and the measuring environment.

First, in the post-correction change amount determining step shown in S331, respective values that are the elapsed time period divided by the interface detection time period are obtained. This value can be thought to be a ratio at which the component, which was detected in the time period, is subjected to concentration, and is referred to as the relative detection time period (i.e., a reciprocal of the correction factor). The slope value as the amount of change per unit time in the optical characteristic value in each time period, is divided by the relative detection time period, and the resulting value, which is the post-correction change amount, is obtained.

Figure 15:
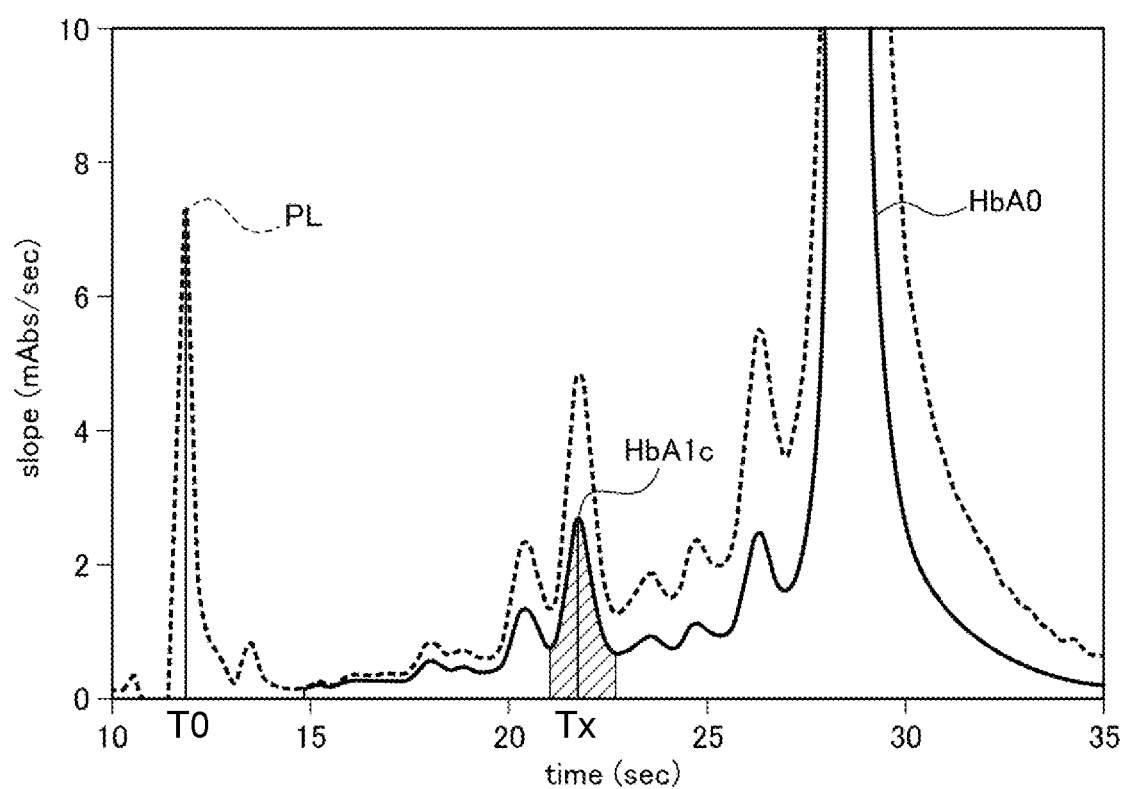
FIG. 15 is an electropherogram obtained on the basis of the differential waveform shown in FIG. 14.

Next, in the electropherogram preparing step shown in S332, an electropherogram is obtained by plotting the post-correction change amounts corresponding to the respective elapsed time periods. The electropherogram obtained on the basis of the differential waveform shown in FIG. 14 is shown in FIG. 15. Note that the differential waveform shown in FIG. 14 is shown by the dashed line for comparison. From FIG. 15, it can be understood that the actual ratio of the component is estimated as being higher than it actually is, since the greater concentration is obtained for the greater elapsed time.

Here, even if the speed difference and the concentration change by the measuring conditions and the measuring environment affecting the moving speed of the hemoglobin component within the capillary channel 27, the amount of change per unit time in the optical characteristic value is corrected by using the relative detection time period that expresses the ratio of the concentration in the measuring environment. Accordingly, the effects of changes in the measuring conditions and the measuring environment on the hemoglobin measured values can be excluded by correcting the amount of change in the optical characteristic value per unit time by the relative detection time period that is the elapsed time period divided by the interface detection time period in the above-described post-correct change amount determining step.

Further, in the peak area deriving step shown in S333, each component of the hemoglobin is identified from the obtained electropherogram, and then the peak area of each component is derived. The fraction having the maximum peak from the interface detection point in time is specified as HbA0. Then, for each peak appearing from the interface detection point in time to the peak of HbA0, the component expressed by the peak is identified by the ratio of the elapsed time period, which is from the interface arrival point in time to the time at which the peak of HbA0 is detected, with respect to the elapsed time from the interface detection point in time to the time when the peak of HbA0 was detected. For example, in FIG. 14, the peak that indicates HbA1c (the hatched region in FIG. 14) is identified in this way.

The amount of each component is derived from the respective peaks identified in this way. A peak identified as a given component is a maximum value, and an area of a fraction including the maximum value can be used as an amount of a component corresponding to the peak. Here, both ends of the fraction can be determined appropriately, and, for example, the both ends may be determined to be minimum values located at either side of the maximum value.

The peak area of each peak may be expressed as a proportion of a fraction including hemoglobin with respect to an entire peak area (an area of the solid line portion in FIG. 14).

Note that, actually, the data each of which is a pair of the elapsed time period and the absorbance is temporarily stored in the storage 84 (see FIG. 4), and the deriving of the peak area is carried out on the basis of the data. Accordingly, for example, the step of obtaining the differential waveform shown in FIG. 14 may be omitted, and the post-correction change amount, which is obtained by dividing the value obtained by differentiating the absorbance over time by the relative detection time period, may be derived directly, and the electropherogram may be prepared on the basis of the post-correction change amount.

Example 1

As Example 1, the hemoglobin separation analysis method of the above-described embodiment was implemented by using human venous blood collected respectively from eight subjects. These samples were referred to as Sample 1 to Sample 8.

(1) Electrophoresis Measurement

Measurement of HbA1c was carried out by capillary electrophoresis using a dilution liquid and a migration liquid including an anionic artificial stationary phase (sodium chondroitin sulfate C).

The sample liquid was diluted by the dilution liquid, and the diluted sample liquid was introduced into the introducing reservoir. Then, voltage was applied to the capillary channel, and electrophoresis was carried out. The electrophoresis was carried out by using constant current control of 67 µA. Then, after the application of the voltage, the absorbance of 415 nm of the migrated sample liquid was acquired by the detector at the downstream side of the capillary channel, at an interval of 20 milliseconds over 40 seconds.

Note that the dilution liquid had the following composition.

citric acid: 40 mM
sodium chondroitin sulfate C: 1% w/v
1-(3-sulfopropyl)pyridinium hydroxide inner salt (Tokyo Chemical Industry): 500 mM
Emulgen LS-110 (Kao): 0.1% w/v
sodium azide: 0.02% w/v The above composition was adjusted to a pH of 6.0 by dimethylaminoethanol for pH adjustment.

Further, the migration liquid had the following composition.

citric acid: 40 mM
piperazine: 20 mM
sodium chondroitin sulfate C: 1.25% w/v
Emulgen LS-110 (Kao): 0.1% w/v
sodium azide: 0.02% w/v The above composition was adjusted to a pH of 5.0 by dimethylaminoethanol for pH adjustment.

(2) Preparation of Electropherogram

The obtained absorbance data were converted into absorbance change amounts per unit time (i.e., the slope values). Thereafter, an electropherogram such as shown in FIG. 14 was obtained with the elapsed time period on the horizontal axis and the slope value on the vertical axis. In the elapsed time period on the horizontal axis, the point (the first point) in time at which the application of the voltage was started was referred to as the reference point of the separation analysis, and as the point in time of 0 seconds.

(3) Correction of Electropherogram

The peak of the 1-(3-sulfopropyl)pyridinium hydroxide inner salt included in the dilution liquid was detected, and the detection time period of the peak was referred to as interface detection time period ($T_0$).

Then, for all of the data from $T_0$ and thereafter of the electropherogram, the respective elapsed time periods of all of the data were divided by $T_0$, and the respective relative detection time periods of all of the data with respect to $T_0$ were derived. This relative detection time period is defined as what is called the reciprocal of the correction factor in the above-described embodiment.

Then, a post-correction change amount was obtained by the following formula for each of all of the data from $T_0$ on of the electropherogram.

post-correction change amount=slope value÷relative detection time period (i.e., the reciprocal of the correction factor)

Then, a corrected electropherogram such as shown in FIG. 14 was obtained with the elapsed time on the horizontal axis and post-correction change amount on the vertical axis.

(4) Derivation of HbA1c Area Ratio

The fraction including hemoglobin corresponding to a total hemoglobin amount, and a fraction including HbA1c, were identified from the corrected electropherogram. Then, an HbA1c area ratio was derived, which is a proportion of the HbA1c peak area (e.g., an area of a peak shown by hatching in FIG. 15) with respect to the total hemoglobin area (e.g., an area of the solid line portion in FIG. 15).

(5) Preparation of Calibration Curve

The HbA1c area ratio of a standard sample, whose HbA1c value, which is the ratio of the HbA1c amount with respect to the total hemoglobin amount, was known in advance, was measured in an environment of 23° C. by the above-described processes (1) to (3). Then, a calibration curve from which the HbA1c value is derived was prepared from the HbA1c area ratio.

(6) Confirmation of Effects of Environmental Temperature

The HbA1c area ratios of the eight samples having different HbA1c values were measured by above-described processes (1) to (4) in environmental temperature conditions of 8° C., 13° C., 23° C., 32° C. and 37° C. Then, the HbA1c value was derived from the calibration curve obtained in above (5). Note that measurement was repeated four times under each one temperature condition for each one sample, and an average value of the results of measurement of these four times was referred to as the measured value. Further, for each of the eight samples, the maximum error, which is defined as a difference between the highest value and the lowest value, was determined.

(7) Comparative Example 1

For the same samples as in Example 1, above process (3) was not carried out, and the HbAc area ratio was derived from an electropherogram that was not corrected by above process (4), and the results are Comparative Example 1.

(8) Results

The results of Example 1 and Comparative Example 1 are shown in following Table 1 and Table 2, respectively. Note the respective numerical values are expressed as percentages.

TABLE 1

| temperature (° C.) | sample | | | | | | | |
|---|---|---|---|---|---|---|---|---|
| | 1 | 2 | 3 | 4 | 5 | 6 | 7 | 8 |
| 8 | 5.16 | 5.98 | 6.89 | 7.81 | 8.53 | 9.57 | 10.39 | 11.31 |
| 13 | 5.11 | 5.86 | 6.84 | 7.76 | 8.61 | 9.67 | 10.55 | 11.23 |
| 23 | 5.15 | 5.86 | 6.83 | 7.66 | 8.59 | 9.56 | 10.39 | 11.16 |
| 32 | 5.16 | 5.92 | 6.87 | 7.67 | 8.57 | 9.42 | 10.39 | 11.12 |
| 37 | 5.16 | 5.99 | 6.73 | 7.72 | 8.61 | 9.38 | 10.20 | 10.85 |
| maximum error | 0.05 | 0.13 | 0.16 | 0.15 | 0.09 | 0.28 | 0.35 | 0.46 |

TABLE 2

| temperature (° C.) | sample | | | | | | | |
|---|---|---|---|---|---|---|---|---|
| | 1 | 2 | 3 | 4 | 5 | 6 | 7 | 8 |
| 8 | 5.21 | 6.03 | 7.00 | 7.90 | 8.68 | 9.72 | 10.54 | 11.51 |
| 13 | 5.16 | 5.92 | 6.90 | 7.82 | 8.68 | 9.74 | 10.71 | 11.38 |
| 23 | 5.15 | 5.85 | 6.83 | 7.66 | 8.59 | 9.53 | 10.41 | 11.20 |
| 32 | 5.15 | 5.87 | 6.81 | 7.61 | 8.51 | 9.34 | 10.33 | 11.01 |
| 37 | 5.10 | 5.91 | 6.68 | 7.61 | 8.46 | 9.27 | 10.08 | 10.71 |
| maximum error | 0.10 | 0.18 | 0.32 | 0.29 | 0.22 | 0.46 | 0.63 | 0.79 |

From Table 1 and Table 2, it can be understood that, in Example 1, the errors in the measured values that were due to changes in the environmental temperature were smaller in all of the samples, as compared with Comparative Example 1. Accordingly, it can be thought that at least the HbA1c value can be measured more accurately by implementing the hemoglobin separation analysis method of the present embodiment.

Example 2

As Example 2, the hemoglobin separation analysis method of the above-described embodiment was implemented by using human venous blood which was collected respectively from six subjects. These samples were referred to as sample 9 to sample 14. Of these samples, samples 9 to 11 were samples that, from a known method for comparison, were known to include HbC by the HbC value that is a ratio of an HbC amount with respect to the total hemoglobin amount. Further, samples 12 to 14 were samples that, from the same known method for comparison, were known to include HbF by an HbF value that is a ratio of the HbF amount with respect to the total hemoglobin amount.

(1) Electrophoresis Measurement

This process was carried out in the same way as in above-described Example 1.

(2) Preparation of Electropherogram

This process was carried out in the same way as in above-described Example 1.

(3) Correction of Electropherogram

This process was carried out in the same way as in above-described Example 1.

(4) Derivation of HbC Value and HbF Value

In samples 9 to 11, the fraction including hemoglobin corresponding to the total hemoglobin amount, and the fraction including HbC were identified from the corrected electropherogram. Then, the HbC area ratio, which is the proportion of the HbC peak area with respect to the total hemoglobin area (e.g., the area of the solid line portion of FIG. 14), was derived, which was referred to as the HbC value. Similarly, in samples 12 to 14, the HbF area ratio, which is the proportion of the HbF peak area with respect to the total hemoglobin area, was derived, which was referred to as the HbF value.

(5) Environmental Temperature

Above-described processes (1) to (4) were respectively carried out under the environmental temperature condition of 23° C. Note that measurement was repeated four times for each sample, and an average value of the results of measurement of these four times was referred to as the measured value.

(6) Comparative Example 2

For the same samples as in Example 2, above process (3) was not carried out, and the HbC value and the HbF value were derived from an electropherogram that was not corrected by above process (4), and the results are Comparative Example 2.

(8) Results

The results of Example 2 and Comparative Example 2 are shown in following Table 3 for the measurement of the HbC values, and in following Table 4 for the measurement of the HbF values, respectively. Note that the respective numerical values are expressed as percentages. Note that, for each of the samples, the measured values that were known in advance from the aforementioned known method for comparison were used herein as well. The respective numerical values are expressed as percentages.

TABLE 3

| measurement method | sample | | |
|---|---|---|---|
| | 9 | 10 | 11 |
| method for comparison | 36 | 36 | 36 |
| Example 2 | 35 | 35 | 36 |
| Comparative Example 2 | 42 | 42 | 42 |

TABLE 4

| measurement method | sample | | |
|---|---|---|---|
| | 12 | 13 | 14 |
| method for comparison | 18 | 6.2 | 39 |
| Example 2 | 17 | 5 | 35 |
| Comparative Example 2 | 12 | 4 | 28 |

From Table 3 and Table 4, it can be understood that, for all of the samples, the HbC values and the HbF values of Example 2 were nearer to the measured values, which were obtained by the method for comparison, as compared with Comparative Example 2. This is because a peak area, which does not include effects of concentration of the sample component, is derived by correction using the correction factor, and the area ratio of each hemoglobin fraction is derived from the peak area. Accordingly, it can be thought that, by implementing the hemoglobin separation analysis method of the present embodiment, even if a calibration curve is not used, the HbC value, which is the ratio of the HbC amount with respect to the total hemoglobin amount, and the HbF value, which is the ratio of the HbF amount with respect to the total hemoglobin amount, can be measured more accurately.

The present invention can be applied to a separation analysis method for hemoglobin in accordance with capillary electrophoresis.

What is claimed is:

1. A separation analysis method for analyzing a sample component included in a sample liquid by introducing the sample liquid into a separation flow path filled with a flow path liquid, the method comprising:
   obtaining a correction factor representing a proportion of a time period from a first point in time when the sample liquid is introduced into the separation flow path, to a second point in time when an interface between the flow path liquid and the sample liquid reaches a predetermined position at the separation flow path, with respect to a time period from the first point in time to a third point in time when an optical characteristic value of the sample component is measured at the predetermined position, and
   correcting the measured optical characteristic value by multiplying the measured optical characteristic value by the correction factor.

2. The separation analysis method of claim 1, wherein the correction factor represents a proportion of a speed at which the sample component flows through the separation flow path, with respect to a speed at which the sample liquid flows through the separation flow path.

3. The separation analysis method of claim 1, comprising correcting an amount of change per unit time in the measured optical characteristic value with the correction factor and obtaining a peak area of a fraction including the sample component from a time distribution of the corrected amount of change per unit time, thereby correcting the measured optical value with the correction factor.

4. The separation analysis method of claim 3, wherein the separation analysis method is a capillary electrophoresis method, the separation flow path is a capillary channel, the flow path liquid is a migration liquid, and the first point in time is a point in time when application of a voltage to the capillary channel is started, and the time distribution is an electropherogram.

5. The separation analysis method of claim 1, comprising obtaining a peak area of a fraction including the sample component from a time distribution of an amount of change per unit time in the measured optical characteristic value and correcting the peak area with the correction factor, thereby correcting the measured value by the correction factor.

6. The separation analysis method of claim 1, wherein the separation analysis method is a capillary electrophoresis method, the separation flow path is a capillary channel, the flow path liquid is a migration liquid, and the first point in time is a point in time when application of a voltage to the capillary channel is started.

7. The separation analysis method of claim 6, wherein
in the capillary electrophoresis, the sample liquid migrates toward a cathode provided at the capillary channel, and
the migration liquid includes an anionic polymer.

8. The separation analysis method of claim 7, wherein the anionic polymer is chondroitin sulfate.

9. The separation analysis method of claim 6, wherein the migration liquid includes an inner salt.

10. The separation analysis method of claim 9, wherein the inner salt is 3-(1-pyridino)propanesulfonate.

11. The separation analysis method of claim 1, wherein the sample liquid is a liquid obtained by diluting blood by a dilution liquid.

12. The separation analysis method of claim 11, wherein the dilution liquid includes an inner salt.

13. The separation analysis method of claim 1, wherein the optical characteristic value is absorbance.

14. The separation analysis method of claim 1, wherein the sample component is hemoglobin.

* * * * *